(12) United States Patent
Chen

(10) Patent No.: US 11,464,517 B2
(45) Date of Patent: Oct. 11, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventor: Zhi Chen, Jiangsu (CN)

(73) Assignee: TOUCHSTONE INTERNATIONAL MEDICAL SCIENCE CO, LTD.

( * ) Notice: Subject to any disclaimer, the term of this patent is extended or adjusted under 35 U.S.C. 154(b) by 263 days.

(21) Appl. No.: 16/957,591

(22) PCT Filed: Dec. 10, 2018

(86) PCT No.: PCT/CN2018/120122
§ 371 (c)(1),
(2) Date: Jun. 24, 2020

(87) PCT Pub. No.: WO2019/128688
PCT Pub. Date: Jul. 4, 2019

(65) Prior Publication Data
US 2020/0345373 A1    Nov. 5, 2020

(30) Foreign Application Priority Data

Dec. 26, 2017 (CN) .......................... 201711434954.3
Dec. 26, 2017 (CN) .......................... 201721846446.1

(51) Int. Cl.
*A61B 17/064* (2006.01)
*A61B 17/115* (2006.01)
(Continued)

(52) U.S. Cl.
CPC ....... *A61B 17/1155* (2013.01); *A61B 17/1114* (2013.01); *A61B 17/326* (2013.01);
(Continued)

(58) Field of Classification Search
CPC .. A61B 2017/00367; A61B 2017/2925; A61B 17/1155
See application file for complete search history.

(56) References Cited

U.S. PATENT DOCUMENTS 4,591,085 A * 5/1986 Di Giovanni ........ A61B 17/072
227/19
5,376,098 A    12/1994 Fontayne et al.
(Continued)

FOREIGN PATENT DOCUMENTS

CN    201098164 Y    8/2008
CN    105310747 A    2/2016
(Continued)

OTHER PUBLICATIONS

International Search Report regarding related PCT App. No. PCT/CN2018/120122; dated Feb. 27, 2019.
(Continued)

*Primary Examiner* — Eyamindae C Jallow
(74) *Attorney, Agent, or Firm* — Dickinson Wright PLLC

(57) ABSTRACT

A handle assembly and a stapler including the same are provided. The handle assembly includes a first handle and a second handle having an un-linked state and a linked state. When the first handle and the second handle are in the un-linked state, and the first handle is rotated in a first direction, the second handle is not rotated, thereby to fire the stapler. When the first handle is in the linked state, and the first handle is rotated in the first direction, the second handle is actuated to rotate in the first direction to fire the stapler. During operation, no matter the stapler is ready to be fired or not, the first handle can be pressed to move by the doctor. However, when the stapler is not ready to be fired, the second handle is not actuated by the first handle, thereby will not fire the stapler.

20 Claims, 37 Drawing Sheets

(51) Int. Cl.
*A61B 17/11* (2006.01)
*A61B 17/326* (2006.01)
*A61B 17/00* (2006.01)
*A61B 17/072* (2006.01)

(52) U.S. Cl.
CPC .............. *A61B 2017/00367* (2013.01); *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 7,658,311 B2 * | 2/2010 | Boudreaux | A61B 17/07207 227/176.1 |
| 7,770,775 B2 * | 8/2010 | Shelton, IV | A61B 17/07207 227/176.1 |
| 9,445,810 B2 * | 9/2016 | Cappola | A61B 17/068 |
| 9,603,599 B2 * | 3/2017 | Miller | A61B 17/1155 |
| 2005/0103819 A1 * | 5/2005 | Racenet | A61B 17/07207 227/175.1 |
| 2013/0175320 A1 * | 7/2013 | Mandakolathur Vasudevan | A61B 17/072 227/175.2 |
| 2016/0331462 A1 * | 11/2016 | Ranucci | A61B 90/03 |
| 2016/0374672 A1 | 12/2016 | Bear et al. | |

FOREIGN PATENT DOCUMENTS

| | | |
|---|---|---|
| CN | 206261635 U | 6/2017 |
| CN | 1969768 A | 8/2017 |
| CN | 106994034 A | 8/2017 |
| EP | 1813201 A1 | 8/2007 |
| JP | 2012024608 A | 2/2012 |
| JP | 2017515528 A | 6/2017 |
| RU | 2025093 C1 | 12/1994 |

OTHER PUBLICATIONS

First Office Action regarding corresponding JP App. No. 2020-535639; dated Jun. 24, 2019.
European Search Report regarding corresponding EP App. No. 18893629.8; dated Sep. 6, 2021.
English Translation of RU Office Action regarding coresponding RU App. No. 2020124374; dated Feb. 11, 2021.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/120122 filed on Dec. 10, 2018, which claims priority to Chinese Patent Applications No. 201711434954.3 and No. 201721846446.1, filed on Dec. 26, 2017, the entire contents of which are incorporated herein by reference.

TECHNICAL FIELD

The present disclosure relates to medical instruments' technology, more particularly, to stapler technology, and specifically to a handle assembly and a stapler including the same.

BACKGROUND

Digestive tract tumor is one of human diseases of high incidence. During treatment a circular stapler is widely used for suturing physiological tissues such as tissues in the digestive tract, instead of the manual operation by doctors. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the proximal end is an end closer to the operator, the distal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the anastomosis.

Along with the technological development, the firing transmission mechanism of the circular stapler has been improved with a lockout mechanism added. Therefore, when the stapler is not ready to be fired, even the doctor presses the handle, the handle cannot be moved for the lockout mechanism, to prevent the stapler from being fired by mistake. However, in practice, the lockout mechanism has some defects. For example, the lockout mechanism has some negative impacts on the operators' experience, and the casing of the stapler may be cracked if the doctor presses the handle vigorously.

SUMMARY

In the light of the problems in the prior art, the object of the present disclosure is to provide a handle assembly and a stapler including the same, to realize that, the first handle can be pressed by the doctor to move no matter whether the stapler is ready to be fired or not, while, the stapler cannot be fired by the first handle through the second handle when the stapler is not ready to be fired, and to prevent the casing from being cracked by pressing the handle vigorously.

In the present disclosure, a handle assembly to fire the stapler is provided, the handle assembly includes a first handle and a second handle. Wherein, the first handle is rotatable relative to the second handle, and the first handle and the second handle have an un-linked state and a linked state. When the first handle and the second handle are in the un-linked state, and the first handle is rotated in a first direction, the second handle is not rotated, and the stapler is configured not to be fired; when the first handle and the second handle are in the linked state, and the first handle is rotated in the first direction, the second handle is rotated along with the first handle in the first direction, to fire the stapler.

In some embodiments, a first end of the first handle is a holding portion, a second end of the first handle is rotatably connected to a first end of the second handle; when the second handle is rotated in the first direction, a second end of the second handle is configured to push a staple pushing rod of the staple, to fire the stapler.

In some embodiments, the first handle and the second handle are rotated around a same center, or, the first handle and the second handle are rotated around two centers, respectively.

In some embodiments, the handle assembly further includes: an indicator, movable between a first position area and a second position area; an elastic portion provided on the first handle, the elastic portion having a first state and a second state, when the indicator is moved from the first position area to the second position area, the indicator being in contact with the elastic portion to actuate the elastic portion to switch from the first state to the second state; wherein, when the elastic portion is in the first state, and the first handle is rotated in the first direction, the elastic portion is not in contact with the second handle, and the second handle is in an insurance position; when the elastic portion is in the second state, and the first handle is rotated in the first direction, the elastic portion is in contact with the second handle to move the second handle from the insurance position to a firing position.

In some embodiments, the indicator is connected to a distal end of a pulling sheet, a proximal end of the pulling sheet is sleeved on a screw rod, a distal end of the screw rod is provided with a knob, when the knob is rotated to move the pulling sheet towards a proximal end of the stapler, the pulling sheet actuates the indicator to move from the first position area to the second position area.

In some embodiments, the first handle is rotatably connected to the second handle through a first pin, and the second handle is rotatably connected to a casing of the stapler through a second pin.

In some embodiments, a first torsion spring and a second torsion spring are sleeved on the first pin and the second pin, respectively, two ends of the first torsion spring are in contact with the first handle and the second handle, respectively, two ends of the second torsion spring are in contact with the second handle and the casing of the stapler.

In some embodiments, the elastic portion includes an elastic cavity having two side walls and having a contracted state and an extended state; when the indicator is move from outside to inside of the elastic cavity, the elastic cavity is actuated to switch from the contracted state to the extended state.

In some embodiments, a first end of the second handle is provided with a second cavity having two side walls; when the first handle is rotated in the first direction, and the elastic cavity is in the contracted state, the elastic cavity is configured to at least partially enter into the second cavity; when the first handle is rotated in the first direction, and the elastic cavity is in the extended state, end surfaces of the side walls of the elastic cavity are in contact with those the second cavity, to prevent the elastic portion from continuing to enter into the second cavity.

In some embodiments, the end surfaces of the side walls of the elastic cavity are first guiding surfaces, having an angle less than 90° relative to the side walls of the elastic cavity, and the end surfaces of the side walls of the second cavity are second guiding surfaces parallel to the first guiding surfaces.

In some embodiments, the elastic cavity includes a contacting section, a protruding section and a guiding section, the protruding section is located between the contacting section and the guiding section, a distance between side walls of the protruding section is less than a width of the indicator, and a distance between side walls at an end of the guiding section is larger than the width of the indicator, to guide the indicator to enter into the protruding section.

In some embodiments, the contacting section, the protruding section and the guiding section of the elastic cavity form an integrated body, and the side walls of the elastic cavity smoothly transit from the protruding section to the guiding section.

In some embodiments, a second end of the first handle is provided with a first cavity, the first cavity and the elastic cavity form an integrated body and are connected with each other.

In some embodiments, the elastic cavity includes a contacting section and an elastic section, a second end of the first handle is provided with a first cavity, the elastic section is inserted into the first handle, while end surfaces of side walls at the contacting section are located outside the first cavity; when the indicator is moved from the outside to the inside of the elastic section, the side walls at the elastic section and the contacting section are all extended towards both sides.

In some embodiments, the elastic cavity further includes a connecting section, the elastic section is located between the contacting section and the connecting section, the connecting section is inserted into the first cavity, and the connecting section is fixed to the first cavity through a fastener.

In some embodiments, the indicator is rotatably fixed to inside of a casing of the stapler, the indicator is rotated from the outside to the inside of the elastic cavity in a second direction, which is in contrary to the first direction.

In some embodiments, the elastic portion includes an elastic sheet, when the indicator is moved from the first position area to the second position area, the elastic sheet is pushed by the indicator to incline towards one side, therefore, when the first handle is rotated in the first direction, the elastic sheet is in contact with the second handle.

In some embodiments, the first handle includes a first cavity having two side walls, the handle assembly further includes: an indicator, movable between a first position area and a second position area; two slots, provided on the first handle and on the two side walls of the first cavity, respectively, each of the slot having a first section and a second section connected with each other; a slider, having two sliding portions corresponding to the two slots and a slider guiding portion in between, the two sliding portions slidably inserted in the corresponding slot, and a return torsion spring for the slider provided between the slider and the second handle; when the indicator is moved from the first position area to the second position area, the slider configured to move from the first section to the second section of the slot, to deform the return torsion spring; wherein, when the slider is in the first section of the slot, and the first handle is rotated in the first direction, the slider is not in contact with the second handle, and, the second handle is in an insurance position; when the slider is in the second section of the slot, and the first handle is rotated in the first direction, the slider guiding portion is in contact with the second handle and actuates the second handle to move from the insurance position to a firing position.

In some embodiment, the second handle includes a second cavity having two side walls, the handle assembly further includes: an indicator, movable between a first position area and a second position area; a rod having a first end connected to the indicator and a second end; two slots, provided on the two side walls of the second cavity, respectively; and a slider, having two sliding portions corresponding to the two slots and a slider guiding portion in between, each of the sliding portions slidably located in the corresponding slot, the slider connected to the second end of the rod, and a return torsion spring for the slider provided between the slider and the first handle; when the indicator is moved from the first position area to the second position area, the slider configured to be moved by the indicator, through the rod, from the first section to the second section of the slot, to deform the return torsion spring; wherein, when the slider is in the first section of the slot, and the first handle is rotated in a first direction, the first handle is not in contact with the slider, and the second handle is in an insurance position; when the slider is in the second section of the slot, and the first handle is rotated in the first direction, the first handle is in contact with the sliding portion and actuates the second handle to move from the insurance position to a firing position.

In some embodiment, the handle assembly further includes a first pin passing through the first handle and the second handle, around which the first handle and the second handle are configured to be rotated.

In the present disclosure, a stapler is provided including the handle assembly as aforementioned.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

BRIEF DESCRIPTION OF THE DRAWINGS

Embodiments of the present disclosure will now be described, by way of example only, with reference to the accompanying schematic drawings, and the other technical features, objects and advantages will be more obvious.

DETAILED DESCRIPTION

In the following, embodiments of the present disclosure will be described in detail with reference to the figures. The concept of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to those skilled in the art fully. Same reference signs in the figures refer to same or similar elements, so repeated description of them will be omitted.

The present disclosure provides a new handle assembly used for firing a stapler. To realize the object as aforementioned, the handle assembly is divided into a first handle 1 rotatable under an external force and a second handle capable of firing the stapler when rotated in a certain direction. Wherein, the first handle and the second handle have an un-linked state and a linked state. When the first handle and the second handle are in the un-linked state, and the first handle is rotated in a first direction, the second handle is not rotated, thereby will not fire the stapler. When the first handle and the second handle are in the linked state, and the first handle is rotated in the first direction, the second handle is rotated along with the first handle in the first direction, to fire the stapler.

Therefore, in the present disclosure, the handle assembly is divided into the first handle and the second handle, and only the movement of the second handle can fire the stapler to execute cutting and suturing actions; during operation, the first handle can be pressed by the doctor to move no matter whether the stapler is ready to be fired or not, while, the stapler cannot be fired by the first handle through the second handle when the stapler is not ready to be fired.

The structure of the handle assembly of the present disclosure will be further described with some embodiments. It should be noted that, the embodiments are described to better illustrate the structure and working state of the handle assembly of the present disclosure, and shouldn't be a limit to the scope of the present disclosure.

First Embodiment

Figure 1:
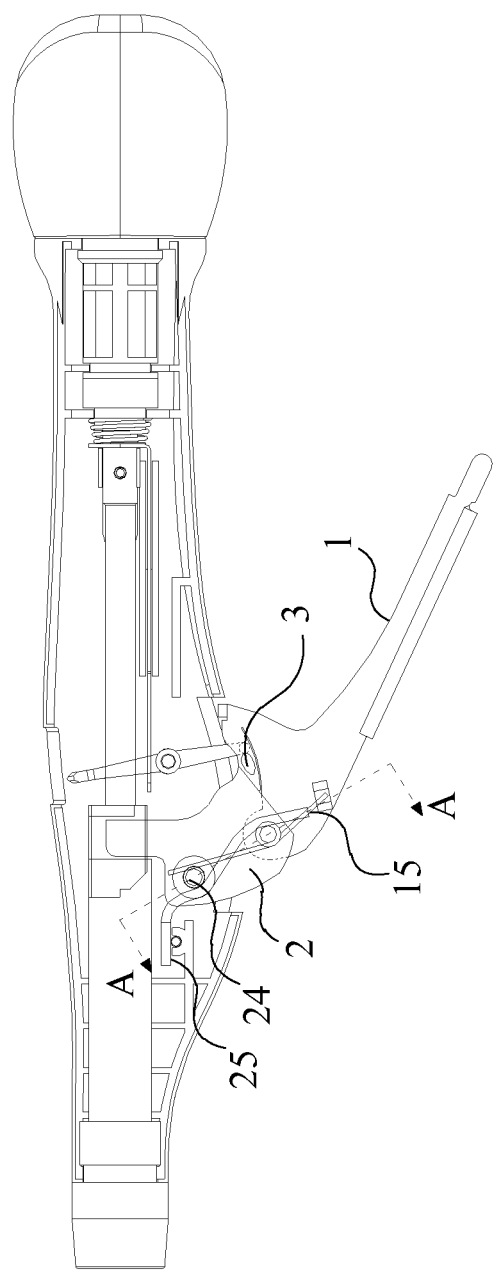
FIG. 1 is a schematic view of a handle assembly used in a stapler according to a first embodiment of the present disclosure.

As shown in FIG. 1, in the first embodiment, the handle assembly further includes an indicator 4 controlling the linkage state between the first handle 1 and the second handle 2.

The indicator has a first end 41, a second end 42 connected to a distal end of a pulling sheet and a fixed end 43. A proximal end of the pulling sheet is sleeved on a screw rod, and a proximal end of the screw rod is connected to a knob. The knob can be rotated to actuate the second end 42 of the indicator to move between a first position area and a second position area through the pulling sheet. Wherein, a window is provided on the instrument body, between the first position area and the second position area, through which the position of the second end 42 of the indicator can be observed during operation. When the second end 42 of the indicator is in the first position area, the stapler is in an insurance state and not ready to be fired. When the second end 42 of the indicator is in the second position area, the stapler is ready to be fired. To give a more obvious indication to the doctor, the second position area L indicating the stapler being ready to be fired is colored green, which is already existed in the prior art.

The first handle 1 is provided with an elastic portion 3. When the second end 42 of the indicator 4 is moved from the first position area to the second position area, the first end 41 of the indicator 4 is in contact with and actuate the elastic portion 3 to switch from a first state to a second state. The first state refers to the state of the elastic portion 3 before being contact with the indicator 4. The second state refers to the state of the elastic portion 3 in contact with the indicator 4.

When the elastic portion 3 is in the first state, and the first handle 1 is rotated in the first direction, the elastic portion 3 is not in contact with the second handle 2, and the second handle 2 is in an insurance position, thereby will not fire the stapler. When the elastic portion 3 is in the second state, and the first handle 1 is rotated in the first direction, the elastic portion 3 is in contact with the second handle 2 to move the second handle 2 from the insurance position to a firing position. At this time, the elastic portion 3 can push the second handle 2 to fire the stapler. In FIG. 1, the first direction refers to a direction anticlockwise.

When the second end 42 of the indicator 4 is in the first position area and the second position area, the movement of the first handle 1 has different effects on the second handle 2. When the second end 42 of the indicator 4 is in the first position area, as the elastic portion 3 is in the first state, the elastic portion 3 will not be in contact with the second handle 2 during moving, and will not apply forces on the second handle 2, therefore, the second handle 2 is still kept in its initial position and will not fire the stapler. When the second end 42 of the indicator 4 is in the second position area, as the elastic portion 3 is in the second state, when the elastic portion 3 is rotated along with the first handle 1, the second handle 2 will be pushed to fire the stapler. Therefore, by changing the position of the indicator 4, the cooperation relationship between the first handle 1 and the second handle 2 can be adjusted.

In summary, when the stapler is not ready to be fired, the second end 42 of the indicator 4 is in the first position area. At this time, the first handle 1 can be rotated easily when pressed by the doctor, while the second handle 2 will not be actuated. Therefore, the stapler is in an invalid firing state, and the first handle can be rotated by a very small force. The doctor can also know the stapler is in the invalid firing state according to the operation experience and the casing of the stapler will not be cracked. When the stapler is ready to be fired, the second end 42 of the indicator 4 is in the second position area, i.e. the area indicating the stapler being ready to be fired. At this time, when the doctor presses the first handle 1, the first handle 1 will actuate the second handle 2 to move, thereby to fire the stapler.

Figure 2:
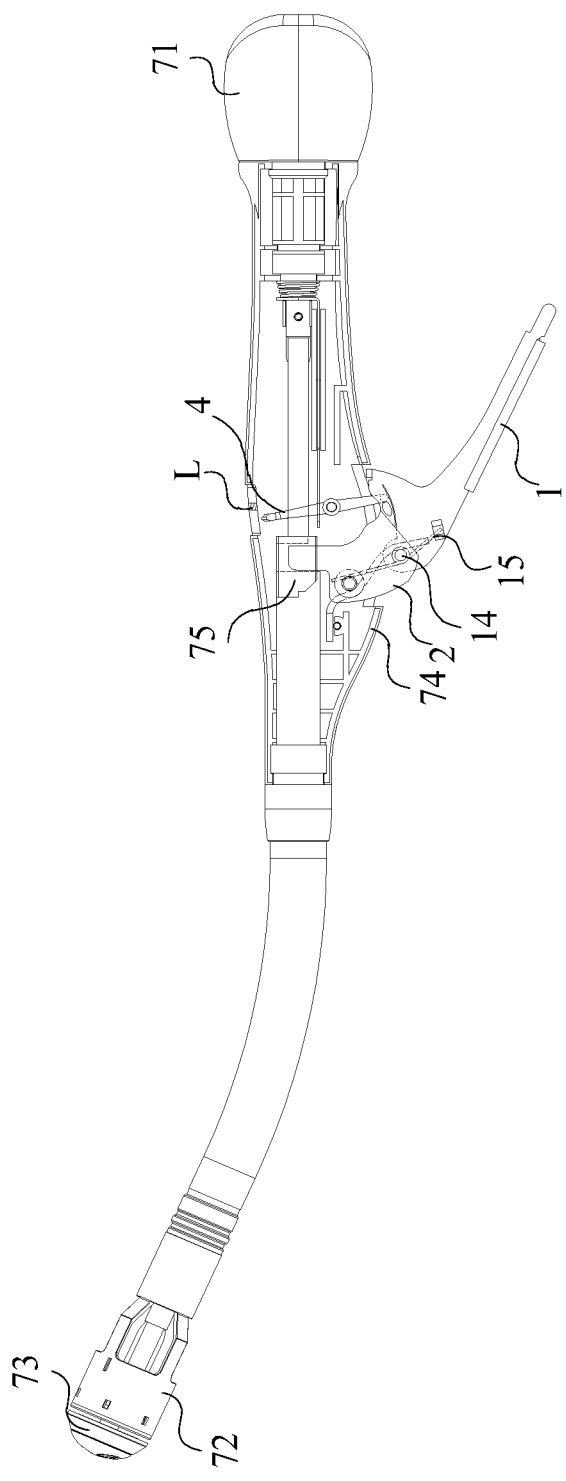
FIG. 2 is a schematic view of a circular stapler according to the first embodiment of the present disclosure.
Figure 3:
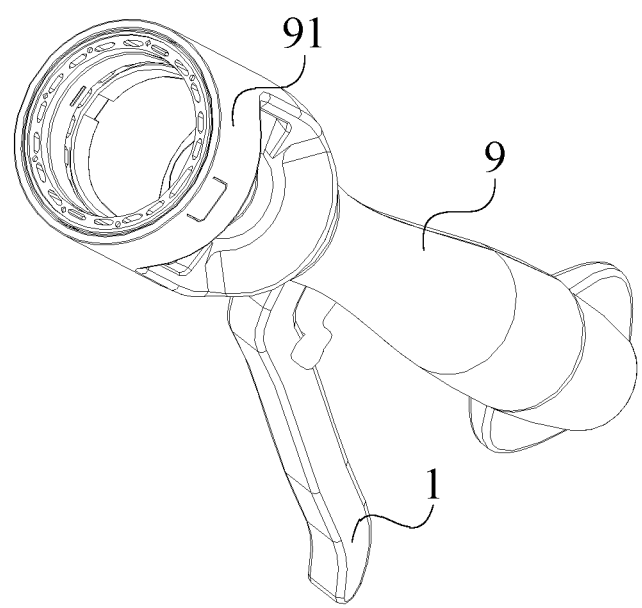
FIG. 3 is a schematic view of the handle assembly used for a circumcision stapler according to the first embodiment of the present disclosure.

FIG. 2 is a schematic view of the handle assembly used for the stapler according to the first embodiment of the present disclosure, in which a circular stapler is shown. One end of the stapler is provided with a cartridge assembly 72 and an anvil assembly 73, the other end of the stapler is provided with a knob 71 and the handle assembly. A second end of the second handle 2 is cooperated with a proximal end of a staple pushing rod 75. When the stapler is ready to be fired, the second handle can push the staple pushing rod 75, to push the staple pushing sheet and circular cutter of the stapler, thereby suturing and cutting issues. FIG. 2 only shows the structure of the stapler as an example, in other embodiments, the handle assembly can also be used in other kinds of staplers to realize the object of the present disclosure. For example, FIG. 3 is a schematic view of an instrument body 9 of a circumcision stapler including the handle assembly. The instrument body 9 of the circumcision stapler includes a cartridge assembly 91, and a glans cap (not shown in the FIGS.) cooperated with the cartridge assembly 91. The second handle 2 is movably connected to one end of the circumcision stapler, the second end of the second handle 2 is cooperated a staple pushing component of the circumcision stapler. When the stapler is ready to be fired, the staple pushing component is pushed by the second handle 2 to fire the circumcision stapler.

In the FIGS. of the present disclosure, to clearly shown the structure of the handle assembly, a casing of the handle assembly is omitted.

Figure 4:
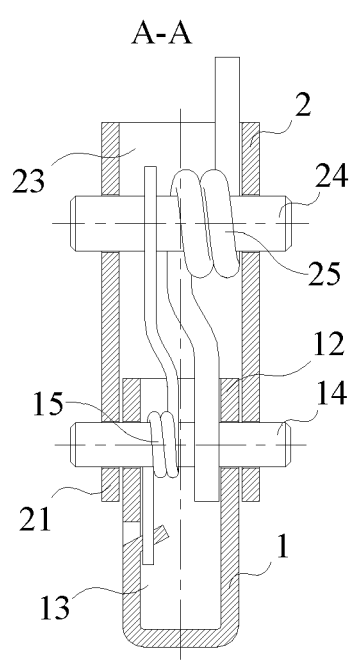
FIG. 4 is a section view along A-A direction of FIG. 1.

FIG. 4 is a section view along A-A direction of FIG. 1 and schematically shows the connecting relationship of the handle assembly according to the first embodiment of the present disclosure. A first end 11 of the handle assembly 1 is a holding portion to be held by the doctor during operation. A second end 12 of the first handle 1 can be rotatably connected to a first end 21 of the second handle 2 through a first pin 14, the second end 22 of the second handle 2 is rotatably connected to the casing 74 of the stapler through a second pin 24. A first torsion spring 15 sleeved on the first pin 14 is located between the first handle 1 and the second handle 2. A second torsion spring 25 sleeved on the second pin 24 is located between the second handle 2 and the casing 74 of the stapler. Therefore, when the elastic portion 3 is in the first state, the stapler is in the insurance state, the first handle can be rotated anticlockwise around the first pin 14 by the operator with a smaller force, and is returned to its initial position clockwise by the first torsion spring 15 after the external force is released. At this time, the second handle is not rotated. When the elastic portion 3 is in the second state, the rotation of the first handle 1 will actuate the second handle 2 to rotate anticlockwise around the second pin 24, and the second handle 2 can be returned to its initial position clockwise by the second torsion spring 25.

The connecting structure between the first handle and the second handle of the handle assembly is only described here as an example. In other embodiments, the first handle and the second handle can be connected in other ways, for example, the quantity of the torsion springs can be decreased or increased, the positions of the torsion springs can be changed etc., which are all within the scope of the present disclosure.

Figure 5:
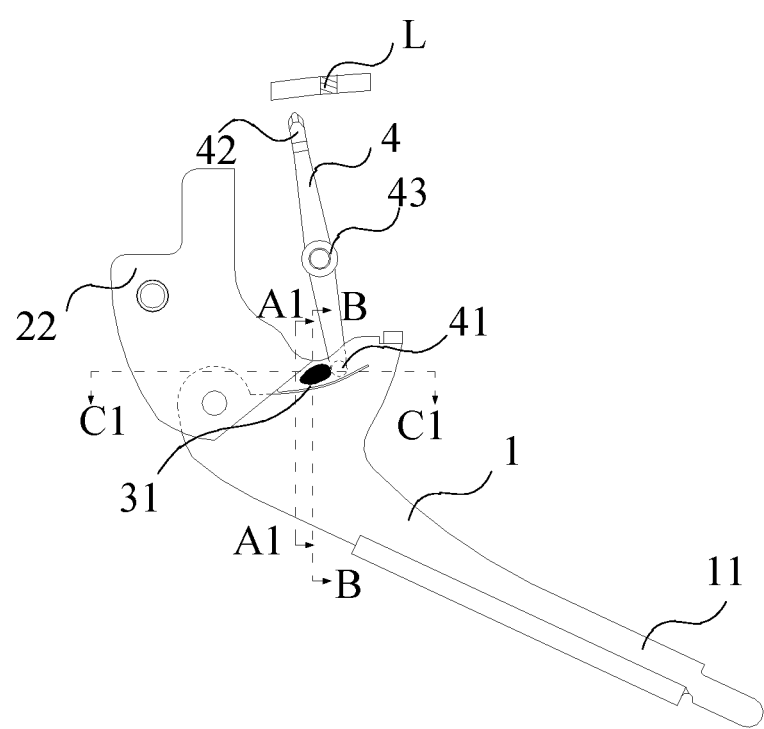
FIG. 5 is a schematic view of the handle assembly when an indicator is outside an elastic portion, and a first handle is not pressed, according to the first embodiment of the present disclosure.
Figure 6:
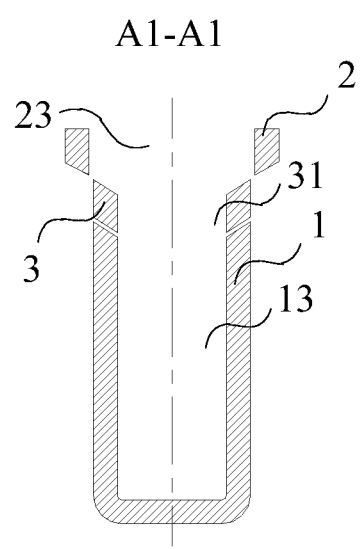
FIG. 6 is a section view along A1-A1 direction of FIG. 5.
Figure 7:
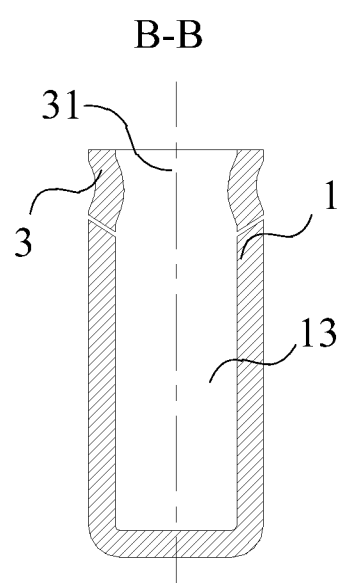
FIG. 7 is a section view along B-B direction of FIG. 5.
Figure 8:
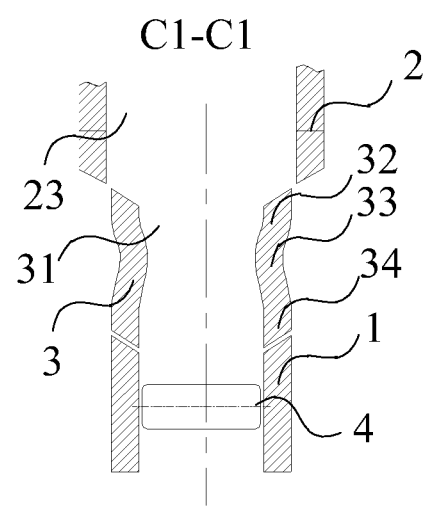
FIG. 8 is a section view along C1-C1 direction of FIG. 5.

FIGS. 5-8 are combined to describe the structure of the elastic portion 3 of the first embodiment of the present disclosure. As shown in FIG. 5, the elastic portion 3 is in the first state, and the first handle 1 is in its initial position. In the first embodiments, the second handle 2 is provided with a second cavity 23, the elastic portion 3 is provided with an elastic cavity 31 having two side walls. When the elastic cavity 31 is in the first state and the second state, the elastic cavity 31 is in a contracted state and an extended state, respectively. When the second end 42 of the indicator is in the first position area and the second position area, the first end 41 of the indicator is outside and inside the elastic cavity, respectively. A width of the indicator 4 is larger than a distance between the side walls of the elastic cavity 31. The width of the indicator 4 refers to the width of the indicator 4 along a direction perpendicular to the side walls of the elastic cavity 31. When the first end 41 of the indicator 4 is moved from the outside to the inside of the elastic cavity 31, the side walls of the elastic cavity are pressed by the indicator 4, to extend towards both sides. FIG. 8 shows the elastic cavity 31 in the contracted state when the first end 41 of the indicator 4 is outside the elastic cavity 31. As shown in FIGS. 5-8, when the elastic cavity 31 is in the contracted state, end surfaces of the side walls of the elastic cavity 31 will not interfere with those of the second cavity 23.

Figure 9:
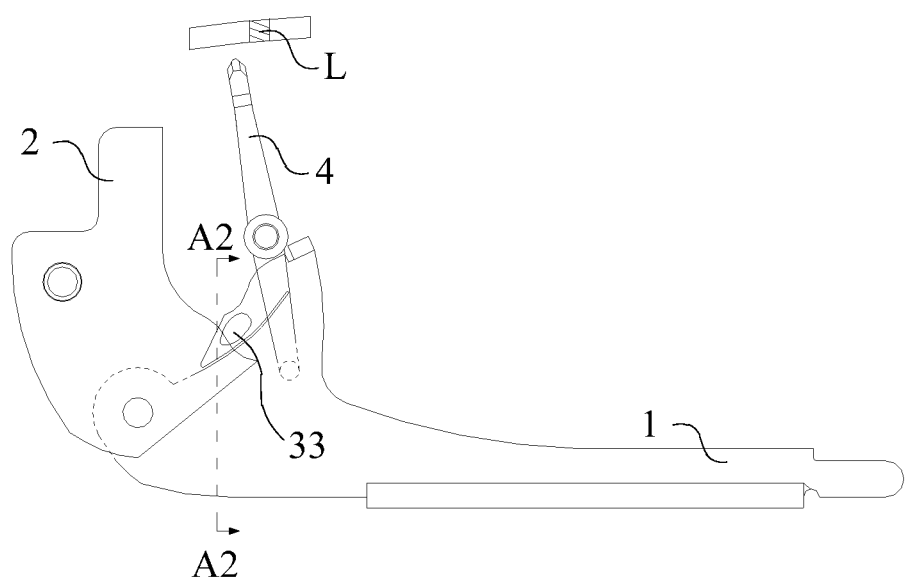
FIG. 9 is a schematic view of the handle assembly when the indicator is outside the elastic portion, and the first handle is pressed, according to the first embodiment of the present disclosure.
Figure 10:
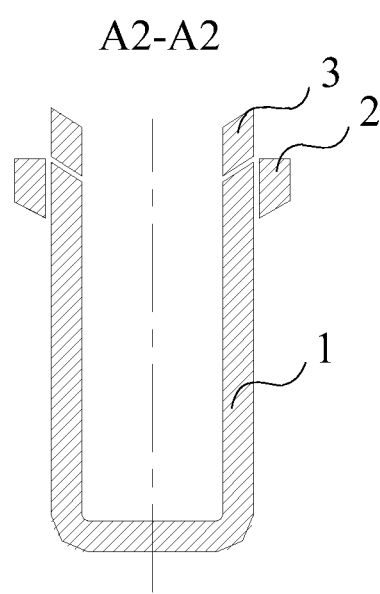
FIG. 10 is a section view along A2-A2 direction of FIG. 9.

As shown in FIGS. 9-10, the elastic portion 3 is in the first state and the first handle 1 is rotated anticlockwise. As the end surfaces of the side walls of the elastic cavity 31 will not interfere with those of the second cavity 23, the elastic portion 3 can at least partially enters into the second cavity 23 (the size of the elastic portion 3 entering into the second cavity 23 varies with degree of pressing). Further, as the degree of pressing is increased, the second end 12 of the first handle 1 can also partially enter into the second cavity 2. Therefore, the first handle 1 will not apply forces on the second handle 2, and the second handle 2 is still kept in the insurance position, thereby will not fire the stapler. As a torsion force of the first torsion spring 15 is much less than a firing force, the force applied on the first handle 1 is only to overcome the torsion force of the first torsion spring 15. The doctor can also get the tactile feedback to know that the indicator 4 is not in the second position area, and the stapler is not fired.

Figure 11:
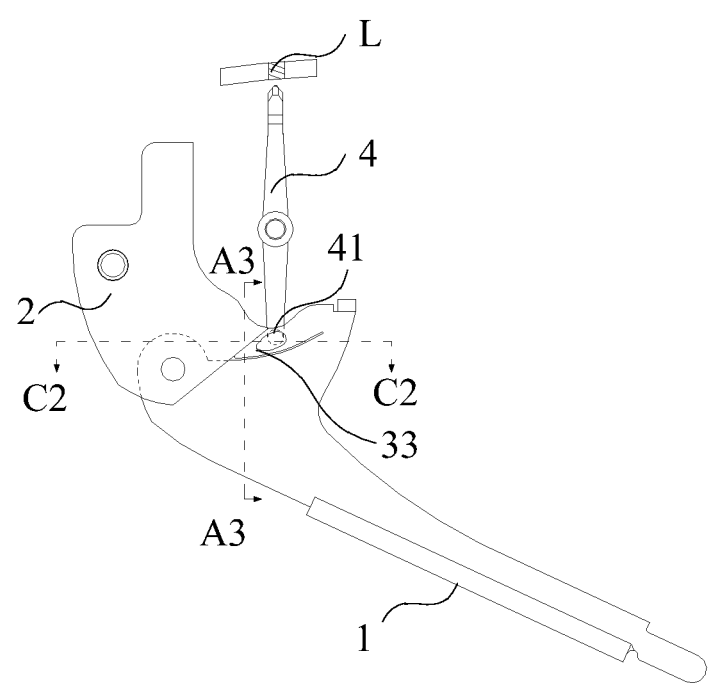
FIG. 11 is a schematic view of the handle assembly when the indicator is inside the elastic portion, and the first handle is not pressed, according to the first embodiment of the present disclosure.
Figure 12:
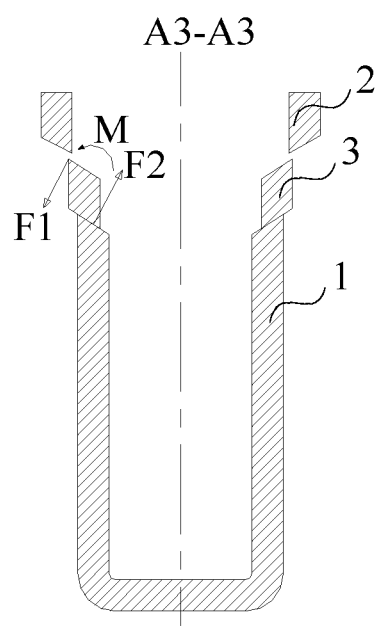
FIG. 12 is a section view along A3-A3 direction of FIG. 11.
Figure 13:
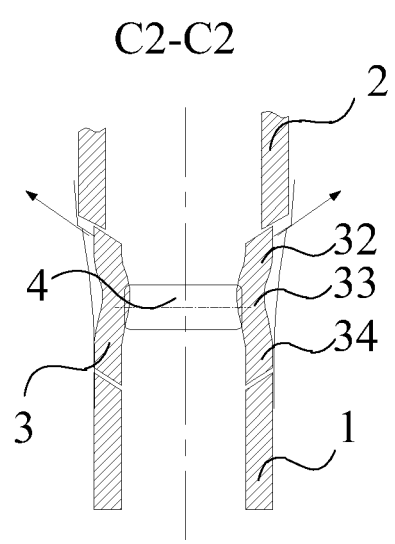
FIG. 13 is a section view along C2-C2 direction of FIG. 11.

As shown in FIGS. 11-13, the elastic portion 3 is in the second state, and the first handle 1 is in its initial position. It can be seen by contrasting FIG. 13 and FIG. 8 that, when the indicator 4 enters the elastic cavity 31, the elastic cavity 31 will be squeezed, to make the side walls of the elastic cavity 31 to extend towards both sides. Therefore, the elastic cavity 31 is switched into the extended state. It can be seen by combining FIG. 12 and FIG. 13 that, at this time, the end surfaces of the side walls of the elastic cavity 31 will interfere with those of the second cavity 23. When contact surfaces between the elastic cavity 31 and the second cavity 23 are moved relative to each other, a force F1 and a force F2 are formed to form a driving torque M for the second handle 2.

Further, as shown in FIG. 13, the elastic cavity 31 can include a contacting section 32, a protruding section 33 and a guiding section 34, and the protruding section 33 is located between the contacting section 32 and the guiding section 34. Side walls at the protruding section 33 protrude towards the inside of the elastic cavity 31, and a distance between side walls at an end of the guiding section 34 is larger than the width of the indicator 4. Therefore, the guiding section 34 is configured for guiding the indicator 4 to enter into the protruding section 33. When the indicator 4 enters into the protruding section 33, the side walls at contacting section 32 and the protruding section 33 are all extended towards both sides. End surfaces of the side walls of the contacting section 32 refer to those of the elastic portion 3. Further, the contacting section 32, the protruding section 33 and the guiding section 34 of the elastic cavity 31 form an integrated body, and the side walls of the elastic cavity 31 smoothly transit from the protruding section 33 to the contacting section 32, to guide the indicator 4 to move smoothly in the elastic cavity 31.

Figure 14:
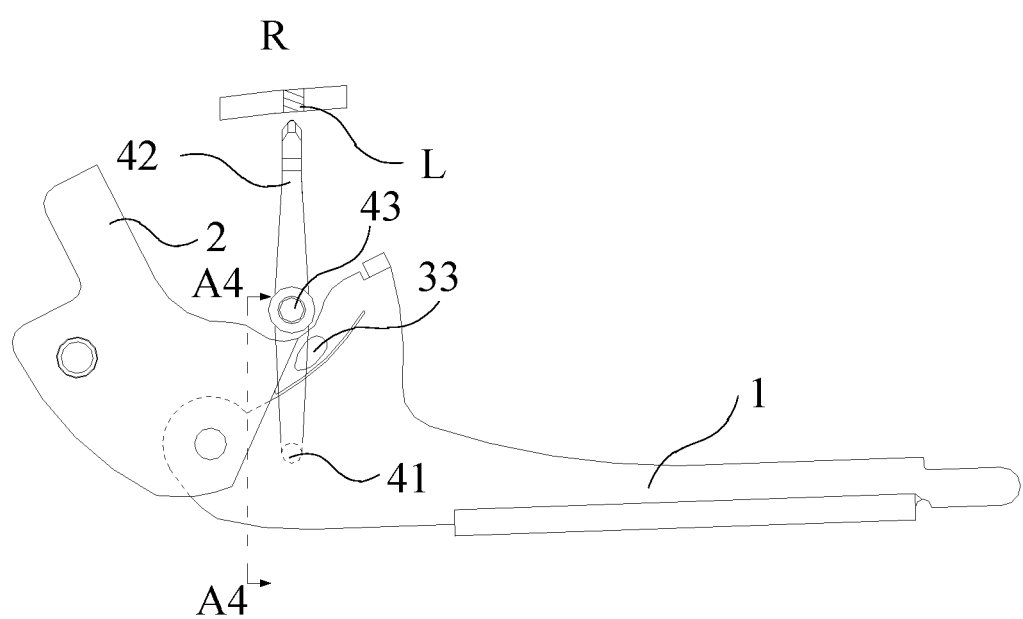
FIG. 14 is a schematic view of the handle assembly when the indicator is inside the elastic portion, and the first handle is pressed, according to the first embodiment of the present disclosure.
Figure 15:
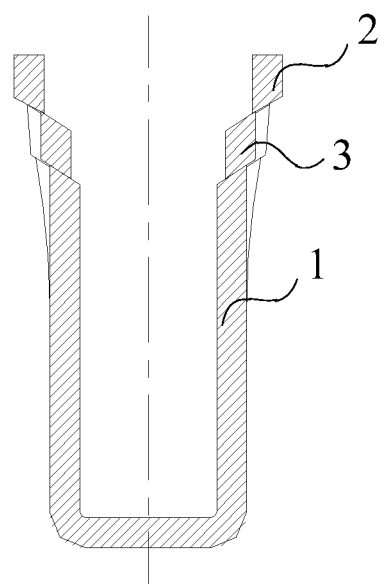
FIG. 15 is a section view along A4-A4 direction of FIG. 14.
Figure 16:
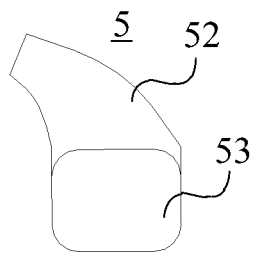
FIG. 16 is a schematic view of an elastic portion according to a second embodiment of the present disclosure.
Figure 17:
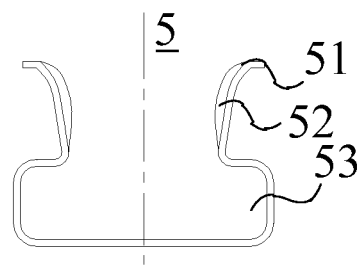
FIG. 17 is a side view of the elastic portion according to the second embodiment of the present disclosure.

As shown in FIG. 14, the elastic portion is in the second state, and the first handle 1 is rotated anticlockwise. The fixed end 43 of the indicator 4 is rotatably fixed to inside of the casing of the stapler, the first end 41 of the indicator 4 is rotated from the outside to the inside of the elastic cavity 31 in a second direction, wherein the second direction is a clockwise direction shown in FIG. 14. The end surfaces of the side walls of the elastic cavity 31 and those of the second cavity 23 are inclined surfaces parallel with each other and used for guiding. Therefore, after the first end 41 of the indicator 4 enters into and opens up the elastic cavity 31, if the first handle is pressed by the doctor, the end surfaces of the side walls of the elastic cavity 31 will apply forces on those of the second cavity 23. Under the forces, the distance between the side walls of the elastic cavity 31 will be larger than that before the first handle is pressed, i.e., larger than the width of the indicator 4. As the first handle 1 continues to rotate, the indicator 4 will depart from the contacting section 32 of the elastic cavity 31. When the firing of the stapler is completed, and the pulling sheet is lifted by the second end of the first handle 1, the indicator is free of the forces from the elastic cavity 31 and is returned to its initial position. When the elastic portion 3 is in the extended state, the end surfaces of the side walls of the elastic cavity 31 will interface those of the second cavity 23. When the elastic portion 3 is moved, the elastic portion 3 will not enter the second cavity 23, but be in contact with and apply forces on the end surfaces of the side walls of the second cavity 23.

The second handle 2 is rotated by the driving torque M, to actuate the second handle 2 to reach the firing position, thereby to fire the stapler.

During firing, the first handle 1 is rotated to lift the pulling sheet, to depart from the indicator 4. The indicator 4 can return to its initial state by a return spring (not shown in the FIGS.). For the reason that the elastic portion 3 is not supported by the indicator 4, when the first handle 1 is released, and the first handle 1 is returned to its initial position clockwise by a returning force of the first torsion spring 15, the second handle 2 will also be returned to the insurance position clockwise by a returning force of the second torsion spring 25.

Further, the end surfaces of the side walls of the elastic cavity 31 are first guiding surfaces having an angle less than 90° relative to the side walls of the elastic cavity 31, and the end surfaces of the side walls of the second cavity 23 are second guiding surfaces parallel to the first guiding surfaces. That is to say, inclined surfaces used for guiding are provided at the corresponding positions of the elastic cavity 31 and the second cavity 23, which will increase an effective cooperation length between the elastic cavity 31 and the second cavity 23 to increase the operation reliability. At the same time, the stapler can be reset after the firing is completed.

Further, the elastic cavity 31 and the second end 12 of the first handle 1 can form an integrated body. For example, a first cavity 13 can be formed on the second end 12 of the first handle 1 by punching press, which is connected with the elastic cavity 31.

As shown in FIG. 14, when the second end 42 of the indicator 4 is in the first position area, the first end 41 of the indicator 4 is not inside the elastic cavity 31, when the second end 42 of the indicator 4 is in the second position area L, the first end 41 of the indicator 4 enters into the elastic cavity 31. After the firing is completed, the second end 42 of the indicator 4 can be returned to the first position area along a direction shown as R in FIG. 14. That is to say, when the first end 41 of the indicator 4 is departed from the inside of the elastic portion 31, the elastic portion 31 is returned to the contracted state and will no longer interfere with the second handle 2. When the external force on the first handle 1 is released, the first handle 1 is returned to its initial position by the first torsion spring 15, and the second handle 2 will be returned to the insurance position by the second torsion spring 25.

Second Embodiment

FIGS. 16-25 are schematic views of a handle assembly according to the second embodiment of the present disclosure. The difference from the first embodiment is that, the elastic portion is provided as an independent component. This is because that forming the elastic portion and the first handle in the integrated body has a high demand in manufacturing process and will bring an increased manufacturing cost.

FIGS. 16-19 show schematically the structure of the elastic portion 5 according to the second embodiment. The elastic portion 5 is provided with an elastic cavity having a contacting section and an elastic section 52, the second end 12 of first handle 1 is provided with the first cavity 13, in which the elastic section 52 is inserted. End surfaces of the contacting section are outside the first cavity 13 as contacting end surfaces 51, and the contracting end surfaces 51 are in contact with the end surfaces of the side walls of the first cavity 13. Similarly, when the indicator 6 is moved from outside of the elastic cavity to inside of the elastic section 52, the side walls at the elastic section 52 and the contacting section extend towards both sides, therefore, the contacting end surfaces 51 also extend towards both sides. Selectively, the elastic cavity further includes a connecting section 53 inserted into and fixed to the first cavity 13, and the elastic section 52 is located between the contacting section and the connecting section 53. The connecting section 53 is fixed to the first cavity 13 through a fastener, for example, the connecting section 53 can be fixed to the first cavity 13 through a hole on the side wall of the first handle 1.

Figure 18:
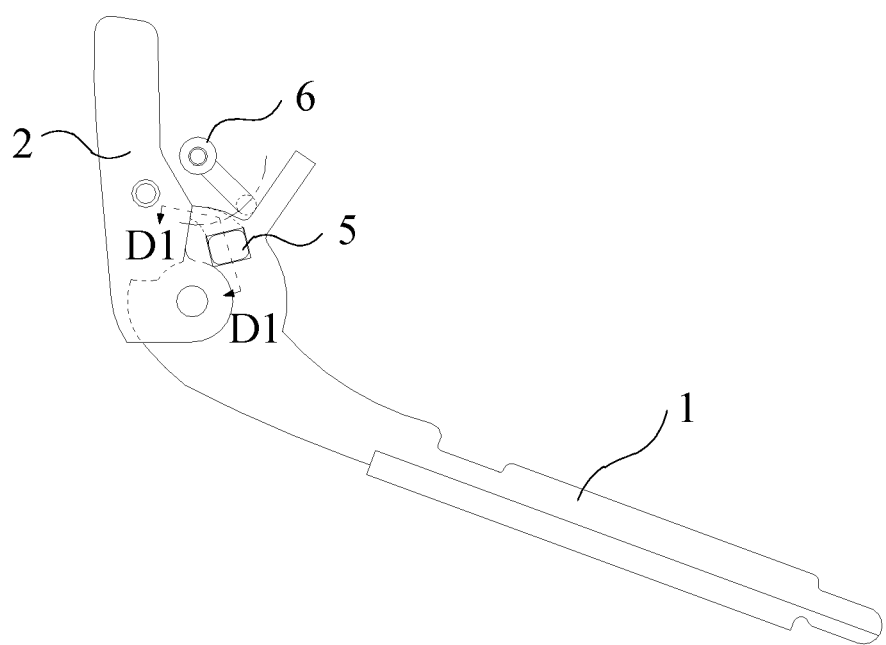
FIG. 18 is a schematic view of the handle assembly when the indicator is outside the elastic portion, and the first handle is not pressed, according to the second embodiment of the present disclosure.
Figure 19:
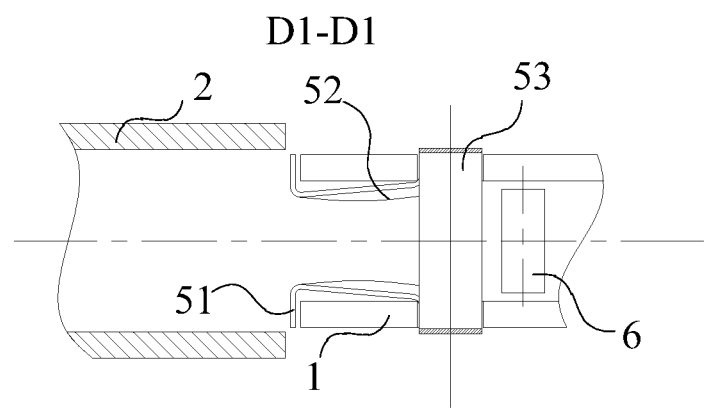
FIG. 19 is a section view along D1-D1 direction of FIG. 18.

FIG. 18 is a schematic view of the handle assembly when the indicator 6 is outside the elastic portion 5 and the first handle 1 is not pressed, according to the second embodiment. At this time, the elastic portion 5 is in the contracted state, and the first handle 1 is in its initial position. FIG. 19 is a section view of FIG. 18 along D1-D1 direction. It can be seen from FIG. 19 that the contacting end surfaces 51 do not interfere with the end surfaces of the side walls of the second cavity 23.

Figure 20:
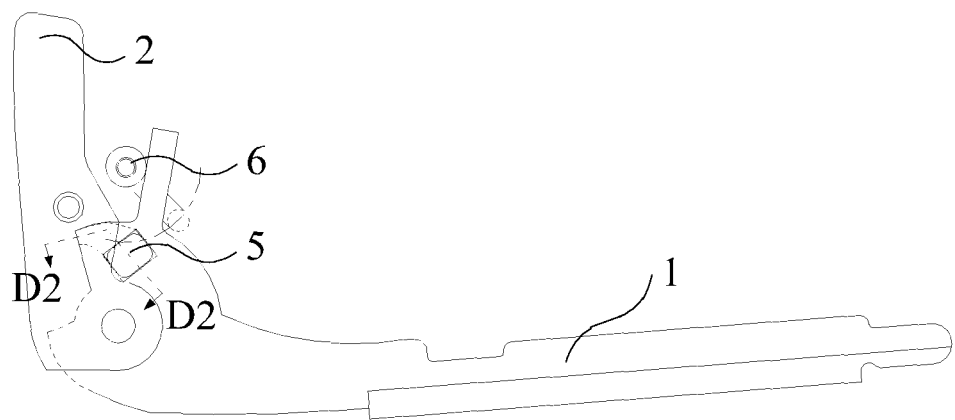
FIG. 20 is a schematic view of the handle assembly when the indicator is outside the elastic portion, and the first handle is pressed, according to the second embodiment of the present disclosure.
Figure 21:
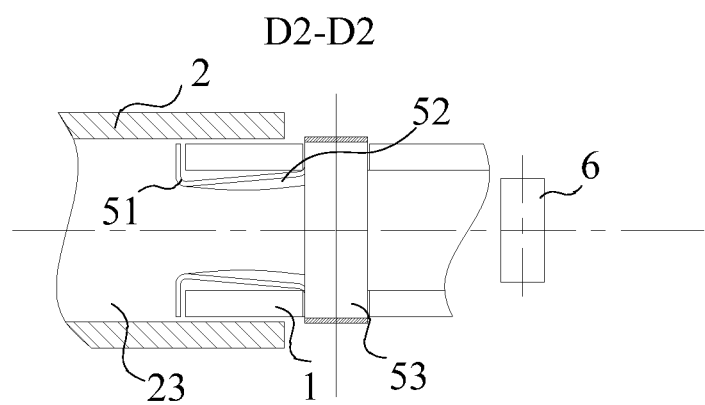
FIG. 21 is a section view along D2-D2 direction of FIG. 20.

FIG. 20 is a schematic view of the handle assembly when the indicator 6 is outside the elastic portion 5 and the first handle 1 is pressed, according to the second embodiment. FIG. 21 is a section view of FIG. 19 along D2-D2 direction. It can be seen from FIG. 22 that, as the contacting end surfaces 51 do not interfere with the end surfaces of the side walls of the second cavity 23, the elastic portion 5 will at least partially enter into the second cavity 23 and will not be in contact with the second handle 2, thereby not pushing the second handle 2 to fire the stapler.

Figure 22:
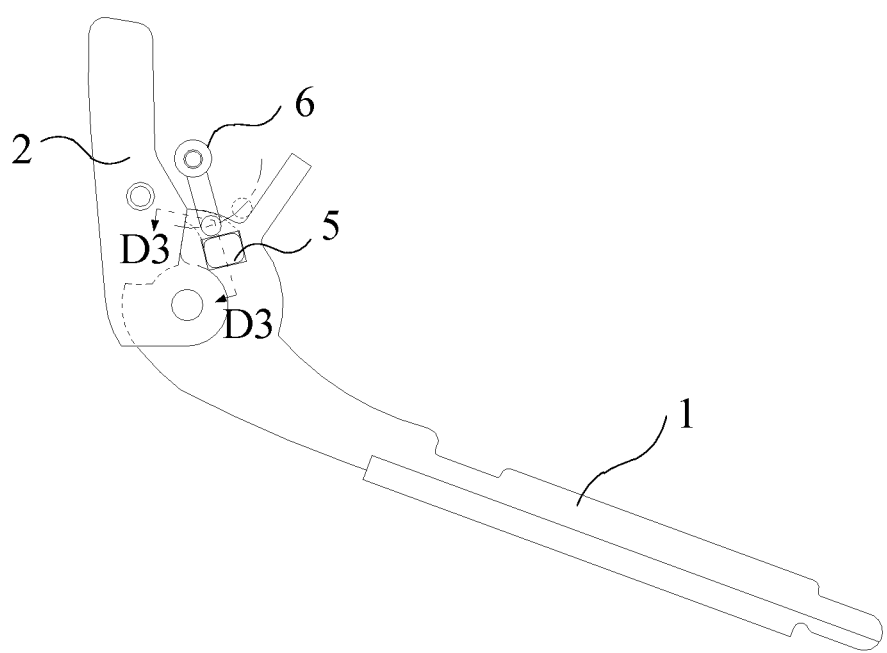
FIG. 22 is a schematic view of the handle assembly when the indicator is inside the elastic portion, and the first handle is not pressed, according to the second embodiment of the present disclosure.
Figure 23:
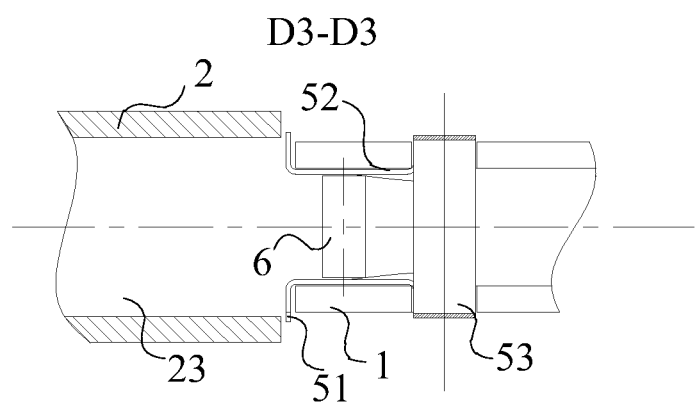
FIG. 23 is a section view along D3-D3 direction of FIG. 22.

FIG. 22 is a schematic view of the handle assembly when the indicator 6 is inside the elastic portion 5 and the first handle 1 is not pressed, according to the second embodiment. At this time, the elastic portion 5 is in the extended state, and the first handle 1 is in its initial position. FIG. 23 is a section view of FIG. 2 along D3-D3 direction. It can be seen from FIG. 23 that the contacting end surfaces 51 interfere with the end surfaces of the side walls of the second cavity 23 to a certain extent.

Figure 24:
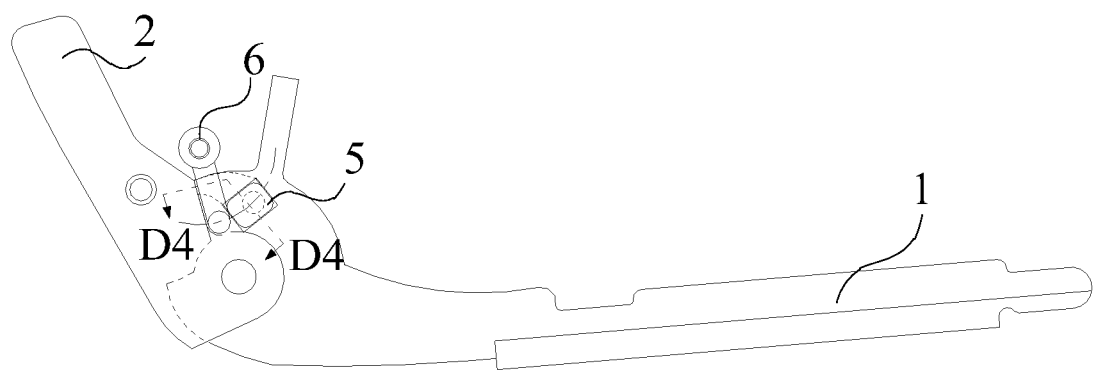
FIG. 24 is a schematic view of the handle assembly when the indicator is inside the elastic portion, and the first handle is pressed, according to the second embodiment of the present disclosure.
Figure 25:
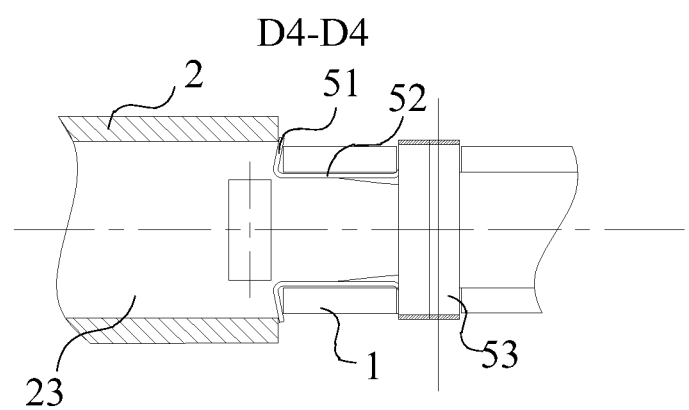
FIG. 25 is a section view along D4-D4 direction of FIG. 24.

FIG. 24 is a schematic view of the handle assembly when the indicator 6 is inside the elastic portion 5, and the first handle 1 is pressed, according to the second embodiment of the present disclosure. At this time, the elastic portion 5 is in the extended state. FIG. 25 is a section view of FIG. 24 along D4-D4 direction. It can be seen from FIG. 25 that, for the reason that the contacting end surfaces 51 of the elastic portion 5 interfere with the end surfaces of the side walls of the second cavity 23, when the elastic portion 5 is moved, the elastic portion 5 won't enter into the second cavity 23, and the contacting end surfaces 51 will push the second handle 2. Therefore, the second handle 2 is moved along with the first handle 1 to the firing position, thereby to fire the stapler.

Third Embodiment

Figure 26:
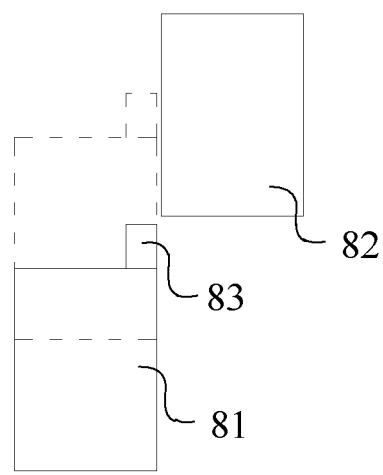
FIG. 26 is a schematic view of an elastic portion of the handle assembly in a first state according to a third embodiment of the present disclosure.
Figure 27:
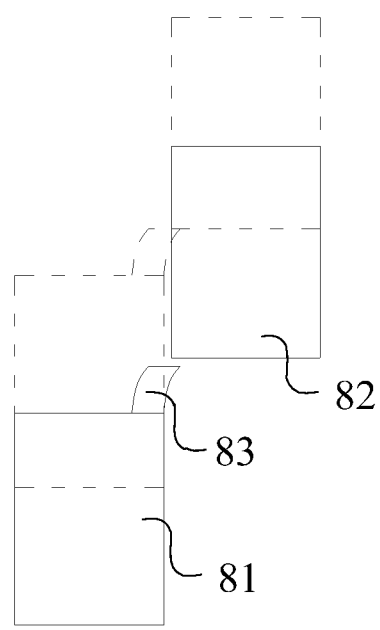
FIG. 27 is a schematic view of the elastic portion of the handle assembly in a second state according to the third embodiment of the present disclosure.

FIGS. 26-27 are schematic views of a handle assembly according to the third embodiment. The difference between the third embodiment and the above two embodiments are that, the elastic portion 83 is an independent solid elastic sheet. FIG. 26-27 only schematically show the influence by the solid elastic sheet on the linkage relationship between the first handle and the second handle. As shown in FIG. 26, when the elastic portion 83 is in the first state, the elastic portion 83 will not interfere with the second handle 82. Therefore, when the first handle 82 is moved (to a position shown in dotted lines in FIG. 26), the elastic portion 83 can be moved along an outer surface of the second handle 82. Therefore, the first handle 81 is not linked with the second handle 82.

As shown in FIG. 27, when the elastic portion 83 is in the second state, the indicator (not shown in FIG. 27) pushes the elastic portion 83 to bend towards one side, and interfere with the second handle 82. When the first handle is moved (to a position shown in dotted lines in FIG. 27), the end portion of the elastic portion 83 will be in contact with the second handle 82, to move the second handle 82 (to a position shown in dotted lines in FIG. 27). When the indicator no longer pushes the elastic portion 83, the elastic portion 83 is returned to its initial state by its own elastic force, thereby no longer interfering with the second handle 82. Under this situation, it's also possible that the second handle 82 is not provided the second cavity, and the first handle 81 is not provided with the first cavity.

In the third embodiment, it's only necessary to link the second handle 81 with the staple pushing rod of the circular stapler. When the second handle 81 is not moved, the staple pushing rod will not be pushed, and when the second handle 81 is moved, the stapler pushing rod is pushed to fire the stapler.

Fourth Embodiment

FIGS. 28-33 schematically show the structure and working process of a handle assembly according to the fourth embodiment. The difference between the fourth embodiment and the first embodiment is that the first handle 1 is not provided with the elastic portion, but a slider 91 and a slot 17. The slot 17 includes a first section and a second section connected with each other, and the slider 91 is slidably located in the slot 17. When the second end 42 of the indicator 4 is moved from the first position area to the second position area, the slider 91 is moved from the first section to the second section of the slot 17. The second handle 2 includes a handle guiding portion 26.

Figure 28:
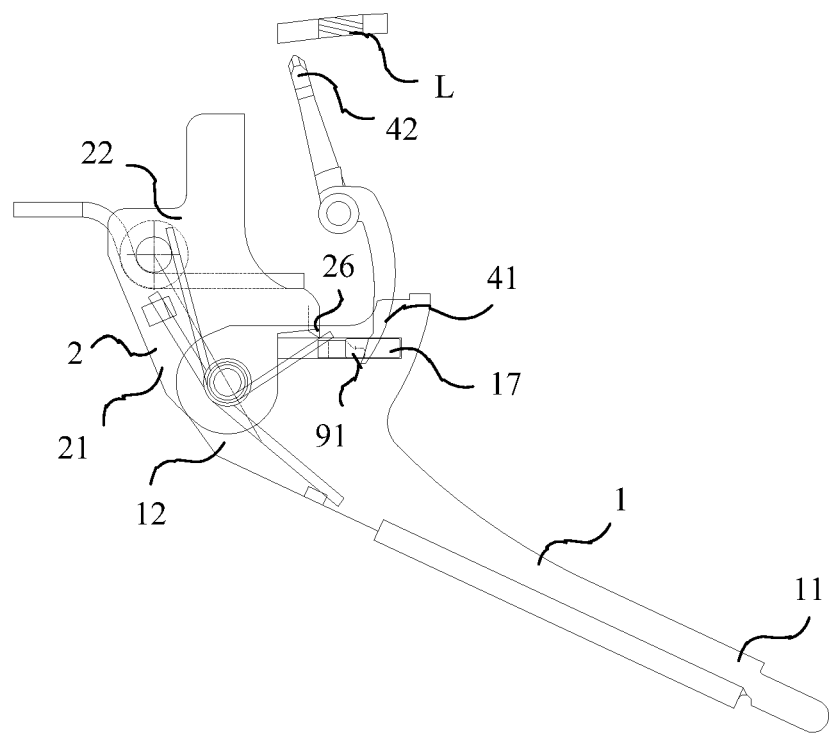
FIG. 28 is a schematic view of a handle assembly in an initial state according to a fourth embodiment of the present disclosure.
Figure 29:
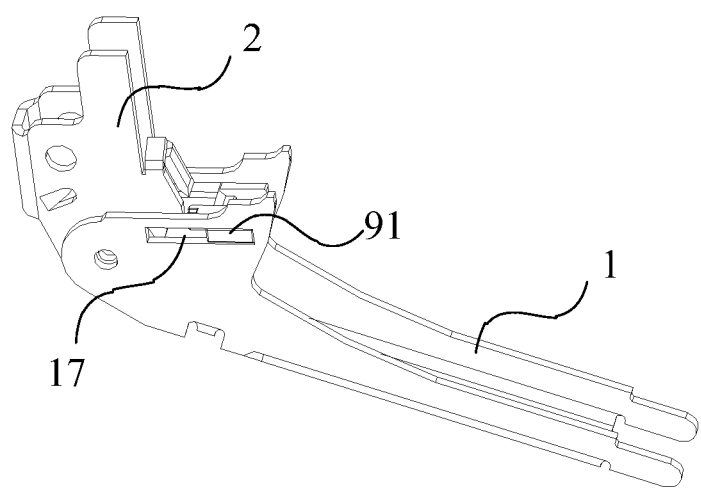
FIG. 29 is a stereogram of the handle assembly according to the fourth embodiment of the present disclosure.
Figure 30:
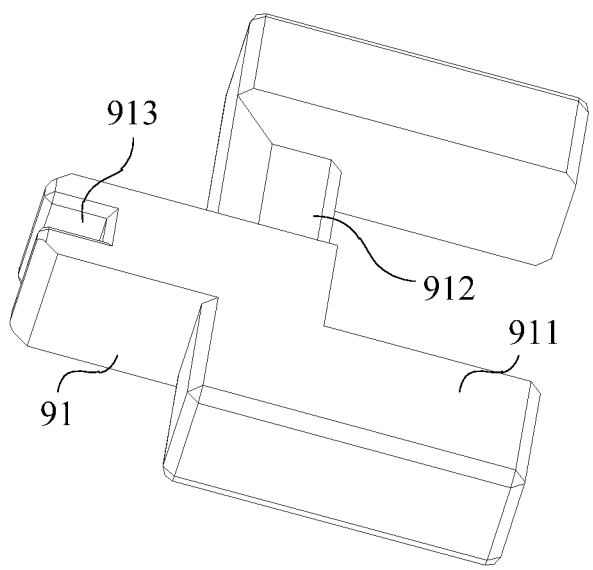
FIG. 30 is a schematic view of a slider according to the fourth embodiment of the present disclosure.

As shown in FIGS. 28-30, the first handle 1 includes a first cavity 13 having two side walls. The slider 91 includes two siding portions 91 on the two ends thereof, a slider guiding portion 912 in between and a limit portion 331 for a torsion spring. A return torsion spring 16 for the slider is provided in the limit portion 331. When the slider is moved from the first section to the second section of the slot 17, the return torsion spring 16 for the slider is deformed.

Figure 31:
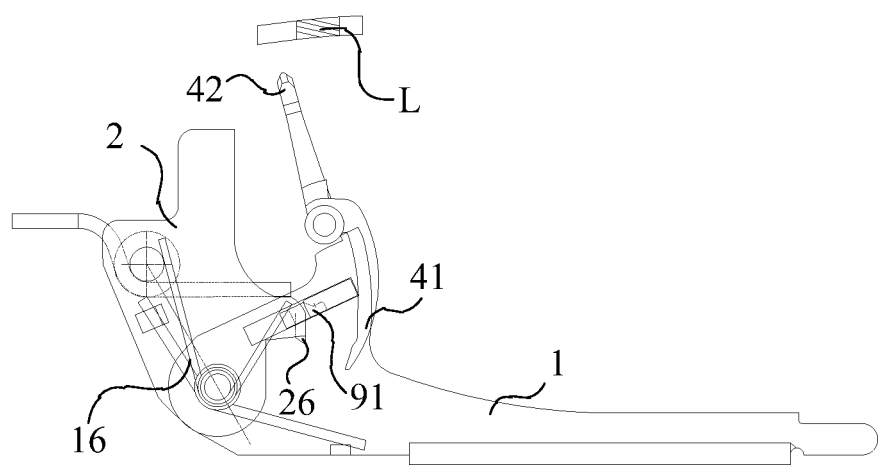
FIG. 31 is a schematic view of the handle assembly in an invalid state according to the fourth embodiment of the present disclosure.

FIG. 31 shows the structure of the handle assembly in an invalid state. At this time, the second end 42 of the indicator 4 is not pulled by the pulling sheet, and outside the area L indicating the stapler being ready to be fired, the slider 91 is in the first section of the slot 17, and the slider guiding portion 912 of the slider 91 will not interfere with the second handle 2. When the first handle 1 is rotated anticlockwise, the first handle 1 and the second handle 2 are not linked, therefore, the second handle 2 is still in its initial position and not rotated. At this time, the first handle 1 can be pressed by the operator without firing the stapler, and the operator can also know the stapler is in the invalid state and not fired, according to the magnitude of his holding force.

It should be noted that, the first section and the second section of the slot 17 in the present disclosure are only relative concepts. As shown in FIGS. 28-33, the first section of the slot 17 is on the right side of the second section of the slot 17.

Figure 32:
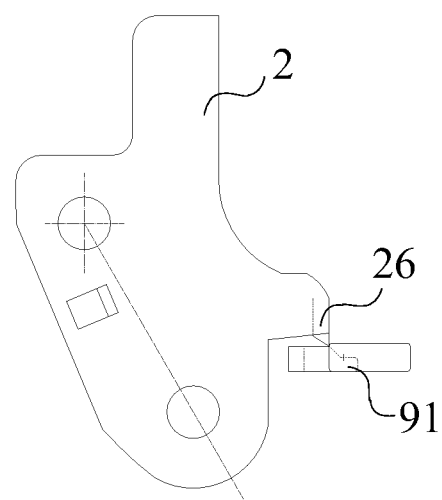
FIG. 32 is a schematic view of the handle assembly in a firing state according to the fourth embodiment of the present disclosure.
Figure 33:
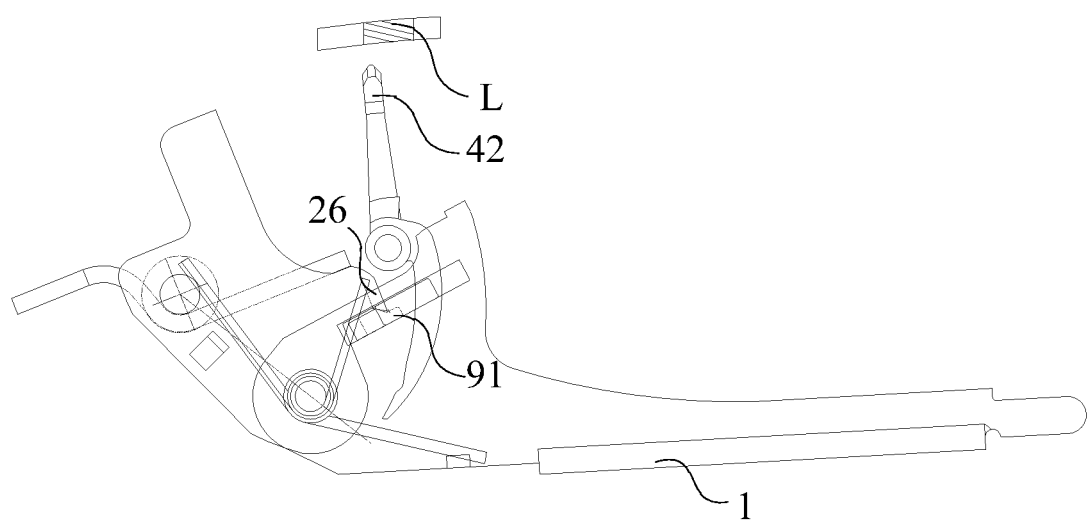
FIG. 33 is a schematic view of the handle assembly in a firing state according to the fourth embodiment of the present disclosure.

FIGS. 32 and 33 show the structure of the handle assembly in a firing state. At this time, the second end 42 of the indicator 4 is pulled by the pulling sheet to enter into the area L indicating the stapler being ready to be fired, and the first end 41 of the indicator 4 actuates the slider 91 to move towards the second section of the slot 17. Therefore, the slider guiding portion 912 will interfere with the second handle 2.

At this time, when the first handle 1 is pressed to rotate anticlockwise, the slider guiding portion 912 will actuate the second handle 2 to rotate anticlockwise, along with the first handle 1. The second end 22 of the second handle 2 pushes the staple pushing rod to fire the stapler. When the pulling sheet is departed from the indicator 4, the indicator 4 is returned to its initial position by the return torsion spring for the indicator (not shown in the FIGS.), and the slider 91 is returned by the return torsion spring 16 for the slider. The returning processes of the first handle 1 and the second handle 2 are the same with those in the first embodiment, and will not be repeated here.

Fifth Embodiment

Figure 34:
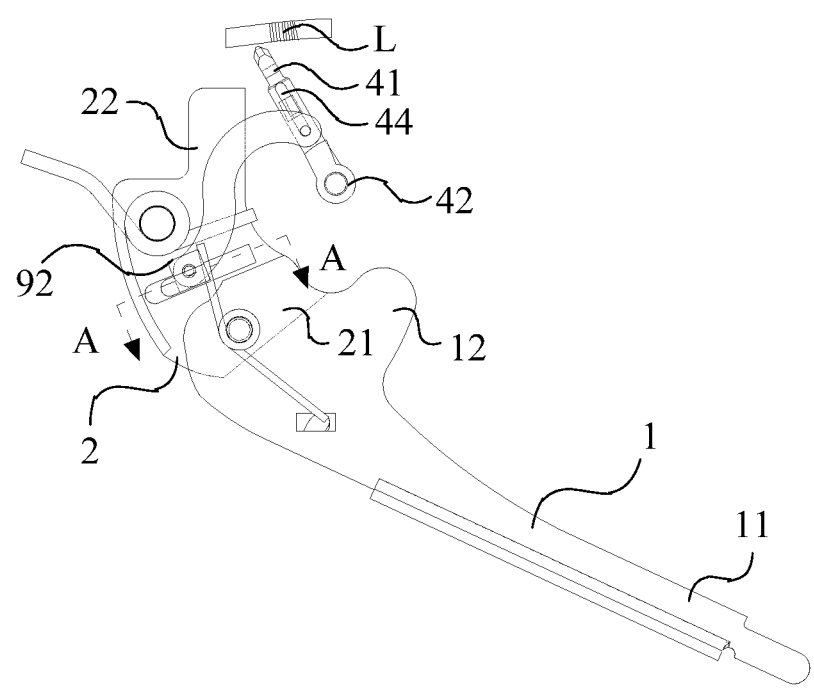
FIG. 34 is a schematic view of a handle assembly in an initial state according to a fifth embodiment of the present disclosure.
Figure 35:
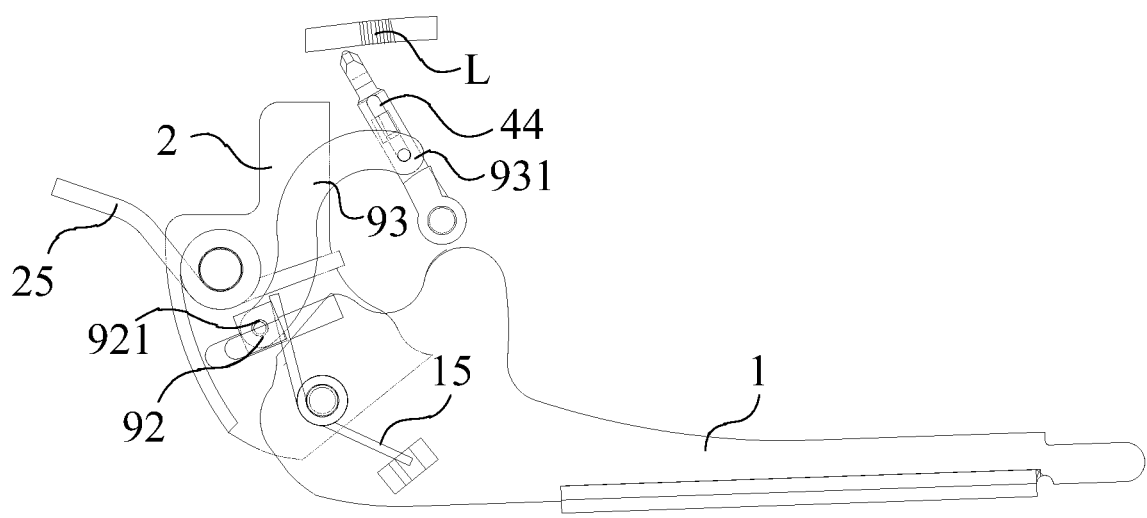
FIG. 35 is a schematic view of the handle assembly in an invalid state according to the fifth embodiment of the present disclosure.

FIGS. 33-35 show the structure and working process of a handle assembly according to a fifth embodiment. The differences between the fifth embodiment and the fourth embodiment are that, the slot 27 is provided on the second handle 2, the first section of the slot 27 is on a left side of the second section, and the first handle 1 is provided with a handle guiding portion (not shown in the FIGS.). The slider 92 is connected to the first end 41 of the indicator 4 by a rod 93, and the first end 41 of the indicator 4 can be rotated around the second end 42 by the pulling sheet. The indicator 4 is provided with a groove 44 for the rod, in which the first end 931 of the rod 93 is slidably located. The second end 932 of the rod 93 is connected to the slider 92 through a connecting pin 921 to pass the force from the indicator 4 to the slider 92. Similarly, the second handle 2 includes a second cavity having two side walls, on which two slots 27 are provided, respectively. The slider 92 includes two sliding portions on both sides and a slider guiding portion (not indicated in the FIGS.) in between. The sliding portions of the slider 92 are inserted in the two slots 27, respectively. A return torsion spring for the slider is further provided between the slider 92 and the first handle 1, to return the slider 92. The first torsion spring 15 can also be directly used as the return torsion spring for the slider 92.

FIG. 35 shows the structure of the handle assembly in the invalid state, according to the fifth embodiment. At this time, the first end 41 of the indicator 4 is not forced by the pulling sheet and outside the area L indicating the stapler being ready to be fired. The rod 93 has no force on the slider 92, and the slider 92 is in the first section of the slot 27. When the first handle 1 is rotated, the second handle 2 is not linked, thereby will not fire the stapler.

Figure 36:
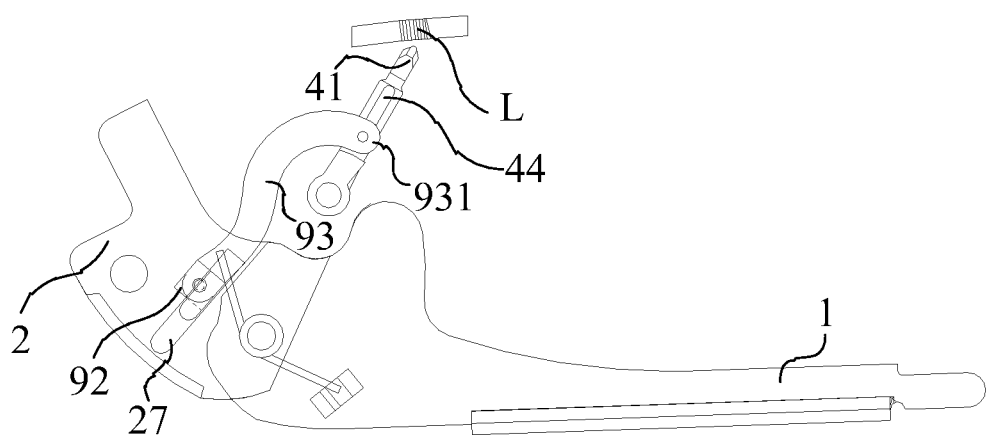
FIG. 36 is a schematic view of the handle assembly in a firing state according to the fifth embodiment of the present disclosure.

FIG. 36 shows the structure of the handle assembly in the firing state according to the fifth embodiment. At this time, the first end 41 of the indicator 4 is pulled by the pulling sheet to enter into the area L indicating the stapler being ready to be fired. The indicator 4 moves the slider 92 though the rod 93, from the first section to the second section of the slot 27. The slider guiding portion interferes with the first handle 1. When the first handle 1 is rotated anticlockwise, it is in contact with the slider guiding portion to rotate the second handle 2 anticlockwise, and the second end 22 of the second handle 2 pushes the staple pushing rod to fire the stapler. When the pulling sheet is departed from the indicator 4, and the indicator 4 is returned to its initial position by the return torsion spring for the indicator (not shown in the FIGS.), the slider 92 will be pushed to return by the returning force of the return torsion spring for the slider. The returning processes of the first handle 1 and the second handle 2 are the same with those in the first embodiment, and will not be repeated here.

Sixth Embodiment

Figure 37:
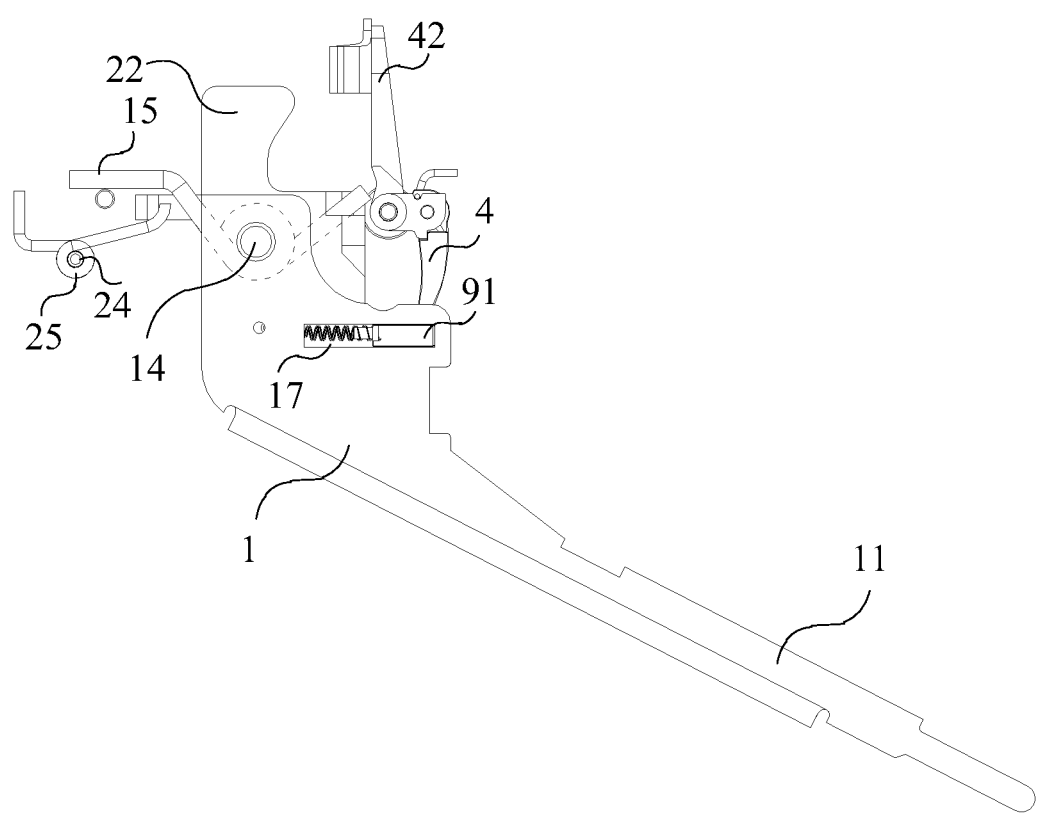
FIG. 37 is a schematic view of a handle assembly according to a sixth embodiment of the present disclosure.

FIG. 37 is a schematic view of a handle assembly according to the sixth embodiment. The differences between the sixth embodiment and the fourth embodiment are that, the first handle 1 and the second handle 2 in the fourth embodiment rotate around two rotation centers while the first handle 1 and the second handle 2 in the sixth embodiment rotate around one rotation center. The first handle 1 and the second handle 2 in the fourth embodiment rotate around the first pin 14 and the second pin 24, respectively, while in the sixth embodiment, the first handle 1 and the second handle 2 are both rotated around the first pin 14. In the sixth embodiment, the first handle 1 and the second handle 2 are both sleeved on the first pin 14, the first torsion spring 15 is sleeved on the first pin 14, and two ends of the first torsion spring 15 are in contact with the second handle 2 and the casing of the stapler, to provide the returning force for the second handle 2. To realize the returning of the first handle 1, a second pin 24 fixed to the casing of the stapler is further provided, on which the second torsion spring 25 is sleeved on. The two ends of the second torsion spring 25 are in contact with the first handle 1 and the casing of the stapler, to provide the returning force for the first handle 1. When the first handle 1 is rotated, the second torsion spring 25 is deformed, and when the second handle 2 is rotated, the first torsion spring 15 is deformed. The other technical features and other working processes of the sixth embodiment are the same with those in the first embodiment, and will not be repeated here.

The present disclosure further provides a stapler including the handle assembly. When the stapler is not ready to be fired, the first handle won't actuate the second handle, thereby will not fire the stapler. The doctor can also judge whether the stapler is fired or not according to his operation experience. Only when the stapler is ready to be fired, the movement of the first handle can actuate the second handle to fire the stapler. Therefore, the stapler is prevented from being fired by mistake, and the casing of the stapler is prevented from being cracked.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A handle assembly for firing a stapler, comprising a first handle and a second handle, wherein, the first handle is rotatable relative to the second handle, and the first handle and the second handle have an un-linked state and a linked state;
when the first handle and the second handle are in the un-linked state, and the first handle is rotated in a first direction, the second handle is not rotated, and the stapler is configured not to be fired;
when the first handle and the second handle are in the linked state, and the first handle is rotated in the first direction, the second handle is rotated along with the first handle in the first direction, to fire the stapler.

2. The handle assembly according to claim 1, wherein, a first end of the first handle is a holding portion, a second end of the first handle is rotatably connected to a first end of the second handle; when the second handle is rotated in the first direction, a second end of the second handle is configured to push a staple pushing rod of the staple, to fire the stapler.

3. The handle assembly according to claim 1, wherein, the first handle and the second handle are rotated around a same center, or, the first handle and the second handle are rotated around two centers, respectively.

4. The handle assembly according to claim 1, further comprising:
an indicator, movable between a first position area and a second position area; and
an elastic portion provided on the first handle, the elastic portion having a first state and a second state, when the indicator is moved from the first position area to the second position area, the indicator being in contact with the elastic portion to actuate the elastic portion to switch from the first state to the second state;
wherein, when the elastic portion is in the first state, and the first handle is rotated in the first direction, the elastic portion is not in contact with the second handle, and the second handle is in an insurance position;
when the elastic portion is in the second state, and the first handle is rotated in the first direction, the elastic portion is in contact with the second handle to move the second handle from the insurance position to a firing position.

5. The handle assembly according to claim 4, wherein, the elastic portion comprises an elastic cavity having two side walls and having a contracted state and an extended state; when the indicator is move from outside to inside of the elastic cavity, the elastic cavity is actuated to switch from the contracted state to the extended state.

6. The handle assembly according to claim 5, wherein, a first end of the second handle is provided with a second cavity having two side walls; when the first handle is rotated in the first direction, and the elastic cavity is in the contracted state, the elastic cavity is configured to at least partially enter into the second cavity; when the first handle is rotated in the first direction, and the elastic cavity is in the extended state, end surfaces of the side walls of the elastic cavity are in contact with those of the second cavity, to prevent the elastic portion from continuing to enter into the second cavity.

7. The handle assembly according to claim 6, wherein, the end surfaces of the side walls of the elastic cavity are first guiding surfaces, having an angle less than 90° relative to the side walls of the elastic cavity, and the end surfaces of the side walls of the second cavity are second guiding surfaces parallel to the first guiding surfaces.

8. The handle assembly according to claim 5, wherein, the elastic cavity comprises a contacting section, a protruding section and a guiding section, the protruding section is located between the contacting section and the guiding section, a distance between side walls of the protruding section is less than a width of the indicator, and a distance between side walls at an end of the guiding section is larger than the width of the indicator, to guide the indicator to enter into the protruding section.

9. The handle assembly according to claim 8, wherein, the contacting section, the protruding section and the guiding section of the elastic cavity form an integrated body, and the side walls of the elastic cavity smoothly transit from the protruding section to the guiding section.

10. The handle assembly according to claim 5, wherein, a second end of the first handle is provided with a first cavity, the first cavity and the elastic cavity form an integrated body and are connected with each other.

11. The handle assembly according to claim 5, wherein, the elastic cavity comprises a contacting section and an elastic section, a second end of the first handle is provided with a first cavity, the elastic section is inserted into the first handle, while end surfaces of side walls at the contacting section are located outside the first cavity;
when the indicator is moved from the outside to the inside of the elastic section, the side walls at the elastic section and the contacting section are all extended towards both sides.

12. The handle assembly according to claim 11, wherein, the elastic cavity further comprises a connecting section, the elastic section is located between the contacting section and the connecting section, the connecting section is inserted into the first cavity, and the connecting section is fixed to the first cavity through a fastener.

13. The handle assembly according to claim 5, wherein, the indicator is rotatably fixed to inside of a casing of the stapler, the indicator is rotated from the outside to the inside of the elastic cavity in a second direction, which is in contrary to the first direction.

14. The handle assembly according to claim 1, wherein, the indicator is connected to a distal end of a pulling sheet, a proximal end of the pulling sheet is sleeved on a screw rod, a distal end of the screw rod is provided with a knob, when the knob is rotated to move the pulling sheet towards a proximal end of the stapler, the pulling sheet actuates the indicator to move from the first position area to the second position area.

15. The handle assembly according to claim 1, wherein, the first handle is rotatably connected to the second handle through a first pin, and the second handle is rotatably connected to a casing of the stapler through a second pin.

16. The handle assembly according to claim 15, wherein, a first torsion spring and a second torsion spring are sleeved on the first pin and the second pin, respectively, two ends of the first torsion spring are in contact with the first handle and the second handle, respectively, two ends of the second torsion spring are in contact with the second handle and the casing of the stapler.

17. The handle assembly according to claim 1, wherein, the elastic portion comprises an elastic sheet, when the indicator is moved from the first position area to the second position area, the elastic sheet is pushed by the indicator to incline towards one side, therefore, when the first handle is rotated in the first direction, the elastic sheet is in contact with the second handle.

18. The handle assembly according to claim 1, wherein, the first handle comprises a first cavity having two side walls, the handle assembly further comprises:
an indicator, movable between a first position area and a second position area;
two slots, provided on the first handle and on the two side walls of the first cavity, respectively, each of the slot having a first section and a second section connected with each other; and
a slider, having two sliding portions corresponding to the two slots and a slider guiding portion in between, the two sliding portions slidably inserted in the corresponding slot, and a return torsion spring for the slider provided between the slider and the second handle; when the indicator is moved from the first position area to the second position area, the slider configured to move from the first section to the second section of the slot, to deform the return torsion spring;
wherein, when the slider is in the first section of the slot, and the first handle is rotated in the first direction, the slider is not in contact with the second handle, and, the second handle is in an insurance position;
when the slider is in the second section of the slot, and the first handle is rotated in the first direction, the slider guiding portion is in contact with the second handle and actuates the second handle to move from the insurance position to a firing position.

19. The handle assembly according to claim 1, wherein, the second handle comprises a second cavity having two side walls, the handle assembly further comprises:
an indicator, movable between a first position area and a second position area;
a rod having a first end connected to the indicator and a second end;
two slots, provided on the two side walls of the second cavity, respectively, each of the slot having a first section and a second section connected with each other; and
a slider, having two sliding portions corresponding to the two slots and a slider guiding portion in between, each of the sliding portions slidably located in the corresponding slot, the slider connected to the second end of the rod, and a return torsion spring for the slider provided between the slider and the first handle; when the indicator is moved from the first position area to the second position area, the slider configured to be moved by the indicator, through the rod, from the first section to the second section of the slot, to deform the return torsion spring;
wherein, when the slider is in the first section of the slot, and the first handle is rotated in a first direction, the first handle is not in contact with the slider, and the second handle is in an insurance position;
when the slider is in the second section of the slot, and the first handle is rotated in the first direction, the first handle is in contact with the sliding portion and actuates the second handle to move from the insurance position to a firing position.

20. A stapler, comprising the handle assembly according to claim 1.

* * * * *